(12) United States Patent
Drexhage et al.

(10) Patent No.: US 6,828,159 B1
(45) Date of Patent: Dec. 7, 2004

(54) CARBOPYRONINE FLUORESCENT DYES

(75) Inventors: Karl-Heinz Drexhage, Schanzenweg 50, 57076 Siegen (DE); Jutta Arden-Jacob, Zirndorf (DE); Jörg Frantzeskos, Wenden (DE); Alexander Zilles, Leeds (GB)

(73) Assignee: Karl-Heinz Drexhage, Siegen (DE)

( * ) Notice: Subject to any disclaimer, the term of this patent is extended or adjusted under 35 U.S.C. 154(b) by 0 days.

(21) Appl. No.: 09/980,531

(22) PCT Filed: Apr. 19, 2000

(86) PCT No.: PCT/EP00/03568

§ 371 (c)(1),
(2), (4) Date: Oct. 26, 2001

(87) PCT Pub. No.: WO00/64986

PCT Pub. Date: Nov. 2, 2000

(30) Foreign Application Priority Data

Apr. 27, 1999 (DE) .......................................... 199 19 119

(51) Int. Cl.[7] ..................... G01N 33/533; G01N 33/545; G01N 33/548; C07K 17/02; C07C 249/00; C07D 221/18; C07D 471/02
(52) U.S. Cl. ........................... 436/546; 435/6; 436/527; 436/529; 436/530; 436/531; 530/391.3; 530/409; 546/56; 546/77; 546/49; 548/418; 548/426; 568/326; 568/632; 564/272; 564/274
(58) Field of Search ................................. 436/546, 527, 436/531, 529, 530; 435/6; 530/391.3, 409; 564/273, 274; 568/326, 632; 548/426, 418; 546/77, 56, 49

(56) References Cited

U.S. PATENT DOCUMENTS 4,320,940 A * 3/1982 Mueller et al.
5,366,860 A 11/1994 Bergot et al.
5,561,045 A * 10/1996 Dorval et al.
6,183,968 B1 * 2/2001 Bandman et al.

FOREIGN PATENT DOCUMENTS

EP 0 543 333 A 5/1993

OTHER PUBLICATIONS

C. Aaron et al, J. Chem. Soc. (1963), pp. 2655–2662.*

C. Barker et al., J. Chem. Soc. [Section B: Physical Organic] (1969), vol. 9, pp. 1068–1071.*

C. Aaron and C.C. Barker: "Steric Effects in Di– and Tri–arylmethane Dyes", Journal of the Chemical Society, No. 2, 1971, pp. 319–324, XP002140950 Chemical Society. Letchworth.

G. Hallas: "Electronic Absorption Spectrum of the alpha–1–Adamantyl Derivative of Michler's Hydrol Blue", Journal of the Chemical Society, No. 1, 1967, pp. 91–92, XP002140951.

R.W. Castelino and G. Hallas: "Electronic Absorption Spectra of Some Analogues and Derivatives of Michler's Ketone", Journal of the Chemical Society, No. 7, 1971, pp. 1468–1471, XP002140952.

* cited by examiner

Primary Examiner—Mary E. Ceperley
(74) Attorney, Agent, or Firm—Henry M. Feiereisen; Ursula B. Day

(57) ABSTRACT

The invention relates to the use of carbopyronine compounds of general formula (I) as marker groups in methods for detecting analytes. The invention also relates to novel carbopyronine compounds and to a method for producing same.

28 Claims, 3 Drawing Sheets

Absorption and fluorescence spectra in ethanol
Fig. 1: AZ 2
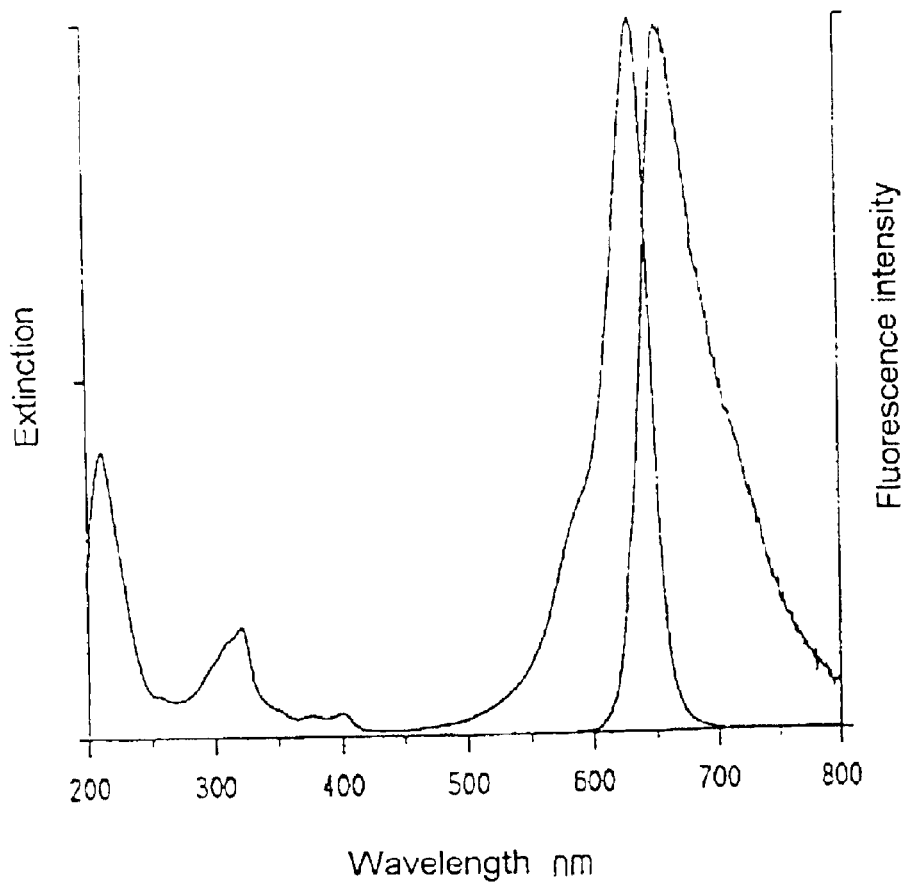

Fig. 2: AZ 13
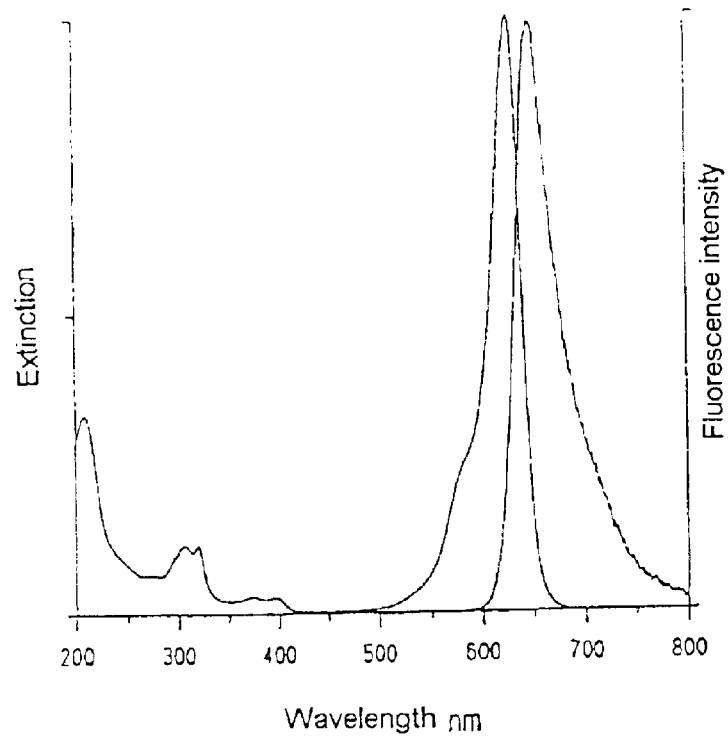
Fig. 3: JA 268
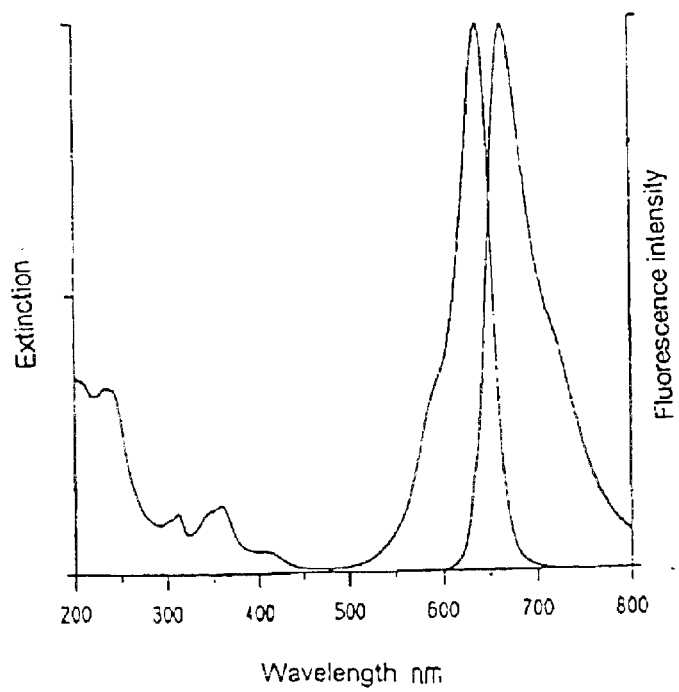

Fig. 4: AZ 11
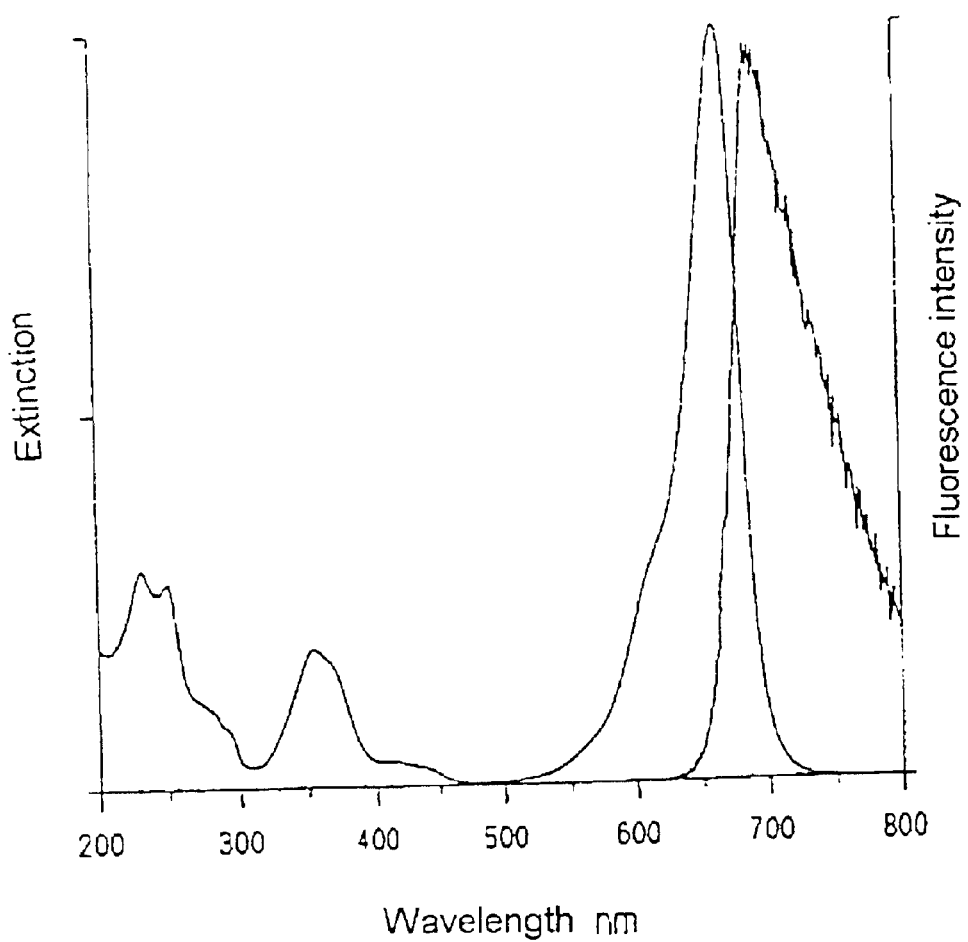

CARBOPYRONINE FLUORESCENT DYES

The invention relates to the use of carbopyronine compounds of the general formula (I) as labeling groups in procedures for the detection of analytes, to novel carbopyronine compounds and to a process for the preparation of these compounds.

In chemical, medical and biological analysis, dyes are used as labeling or detection groups. In particular, fluorescent dyes have gained importance in recent years and displaced other often cost-intensive procedures, which use, for example, radioisotopes for labeling.

In particular in the field of DNA sequencing, fluorometric procedures have gained acceptance in recent years and almost completely replaced the procedures customary up till then, which use radioactive isotopes.

In spite of the availability of various fluorescent dyes, such as, for example, FITC (fluorescein isothiocyanate), FLUOS (fluorescein N-hydroxysuccinimide ester), rhodamine derivatives etc., it was previously not possible to solve the problems due to background fluorescence, nonspecific binding phenomena and the need for cost-intensive measuring equipment in a satisfactory manner.

As a result of background fluorescence and nonspecific binding, the sensitivity and accuracy of the measurements is reduced. In addition, in the case of available fluorescent dyes the absorption maximum lies in regions which do not make possible the use of light sources which are less expensive and which can be of small dimensions, such as, for example, He/Ne lasers and laser diodes.

An object of the present invention was thus to make available fluorescent dyes which can be employed as labeling groups in procedures for the detection of analytes and at least partially avoid the disadvantages of the prior art.

This object has been achieved by the use of compounds of the general formula (I)

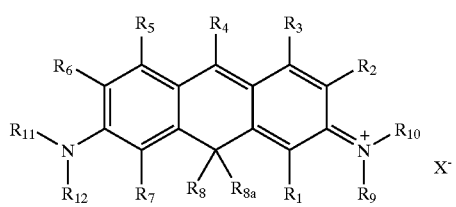

I as labeling groups in a procedure for the detection of an analyte, where $R_1$, $R_2$, $R_3$, $R_4$, $R_5$, $R_6$ and $R_7$ are in each case independently hydrogen, halogen, a hydroxyl, amino, sulfo or carboxyl or aldehyde group or a saturated or unsaturated, straight-chain, branched or cyclic hydrocarbon group having up to 20 C atoms, where the hydrocarbon groups include alkyl, alkenyl, alkynyl, cycloalkyl, aryl, in particular phenyl, or/and heteroaryl radicals and optionally heteroatoms such as oxygen, sulfur or nitrogen atoms or/and two or more substituents, preferably selected from halogens, hydroxyl, amino, sulfo, phospho, carboxyl, aldehyde, $C_1$–$C_4$-alkoxy or/and $C_1$–$C_4$-alkoxycarbonyl groups, or one or more of the radicals $R_1$–$R_7$, in each case with adjacent substituents, form a ring system which can contain one or more multiple bonds, $R_8$ and $R_{8a}$ in each case independently are a saturated or unsaturated, straight-chain, branched or cyclic hydrocarbon group having up to 20 carbon atoms, e.g. a $C_1$–$C_6$-alkyl group, in particular methyl, ethyl, propyl or/and butyl, or an aryl or heteroaryl group, in particular phenyl, which optionally contain heteroatoms such as oxygen, sulfur or nitrogen atoms or/and one or more substituents, preferably selected from halogens, hydroxyl, amino, sulfo, phospho, carboxyl, aldehyde, $C_1$–$C_4$-alkoxy or/and $C_1$–$C_4$-alkoxycarbonyl groups, or $R_8$ and $R_{8a}$ can form a ring system, $R_9$, $R_{10}$, $R_{11}$ and $R_{12}$ in each case independently are hydrogen or a saturated or unsaturated, straight-chain, branched or cyclic hydrocarbon group having up to 20 C atoms, e.g. polyether, phenyl, phenylalkyl having 1–3 C atoms in the chain, where the hydrocarbon groups can optionally contain heteroatoms such as oxygen, sulfur or nitrogen atoms or/and one or more substituents, preferably selected from halogens, hydroxyl, amino, sulfo, phospho, carboxyl, carbonyl, alkoxy or/and alkoxycarbonyl groups, or one or more of the radicals $R_9$–$R_{12}$, in each case with adjacent substituents, form a ring system which can contain one or more multiple bonds, where —N($R_{11}$)($R_{12}$) or/and =($R_9$)($R_{10}$) can be replaced by —OR$^9$ or/and =O, and X is optionally anions present for charge equalization.

The compounds of the general formula (I) can be employed as labeling groups in procedures for the qualitative or/and quantitative determination of an analyte. This determination can be carried out in aqueous liquids, e.g. samples of body fluids such as, for example, blood, serum, plasma or urine, wastewater samples or foodstuffs. The procedure can also be carried out as a wet test, e.g. in a cuvette, or as a dry test in an appropriate reagent carrier. The determination of the analyte can be carried out here by means of a single reaction or by means of a sequence of reactions. Surprisingly, the use of compounds of the general formula (I) showed very good results in chemical and in particular in medical and biological detection procedures for the determination of an analyte, especially in nucleic acid sequencing procedures and in protein analysis.

The compounds of the general formula (I) can be used in all chemical, medical and biological detection procedures known to the person skilled in the art in which fluorescent dyes are suitable as labeling groups. For this, the compounds of the general formula (I) are in general coupled covalently to a receptor which is specific for the analyte to be detected. This takes place using generally known procedures. The specific receptor can be any suitable compound or any suitable molecule, preferably it is a peptide, a polypeptide or a nucleic acid. The compounds or conjugates of these compounds can be used, for example, in nucleic acid, hybridization procedures, in particular for the sequencing of nucleic acids or immunochemical procedures. Procedures of this type are described, for example, in Sambrook et al., Molecular Cloning, A Laboratory Manual, 1989, Cold Spring Harbor.

A further object of the present invention was to make available novel carbopyronine compounds which are suitable in particular for use as labeling groups in analyte detection procedures, can be prepared using simple and inexpensive processes, can be handled without problems and at least partially avoid the disadvantages of the prior art.

This object has been achieved by a compound of the general formula (I)

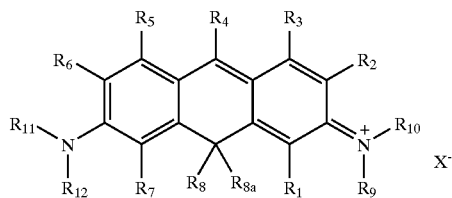

where
- $R_1$–$R_{12}$ and X have the meanings indicated above,
- with the proviso that if $R_1$–$R_3$ and $R_5$–$R_7$ are hydrogen and $R_8$, $R_{8a}$ and $R_9$–$R_{12}$ are methyl,
- $R_4$ is not hydrogen, methyl, isopropyl, phenyl, 2,6-dimethylphenyl or 2-isopropenylphenyl.

An advantage of the compounds (I) is that owing to an almost arbitrary substituent variation the properties of individual compounds, e.g. the spectroscopic properties, the position of the absorption and fluorescence maxima, the solubility properties, the fluorescence quantum yield and decay time, vary strongly and thus can be selected as desired. In this way, interferences with interfering substances in samples such as serum, blood or plasma etc. can be reduced or even avoided completely. The preparation of some compounds of the formula (I) can be carried out by processes known per se. Preferably, the synthesis is carried out, however, according to a novel process described below, which is particularly simple and inexpensive.

In a preferred class of the compounds (I), $R_6$ is bridged with $R_{11}$ or/and $R_7$ with $R_{12}$, $R_1$ with $R_{10}$ or/and $R_2$ with $R_9$ and form a ring system which can contain one or more multiple bonds. The ring system preferably contains one or more 5- or 6-membered rings.

$R_4$ is preferably hydrogen, $C_1$–$C_6$-alkyl or a radical containing an aromatic ring system, e.g. a radical containing a carboxyl or/and halogen group, such as 2-carboxyphenyl, 2-carboxytetrachlorophenyl or pentafluorophenyl. $R_8$ and $R_{8a}$ are preferably in each case independently methyl, ethyl or/and optionally substituted phenyl.

Examples of particularly preferred classes of compound are shown in the general formulae IVa to IVe:

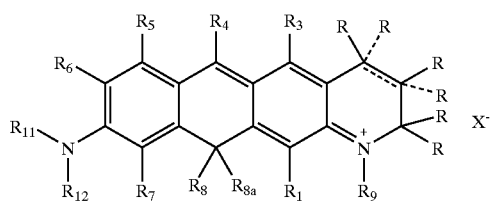

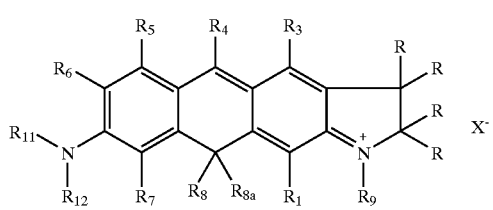

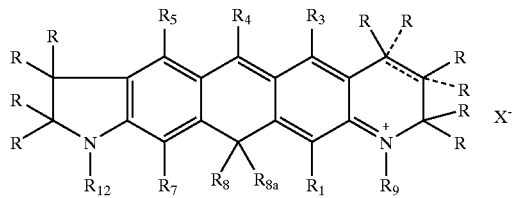

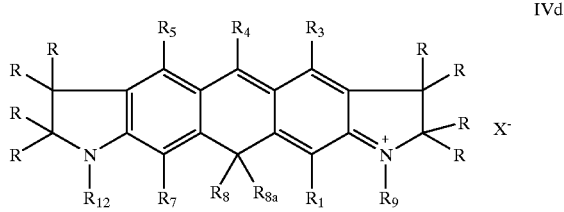

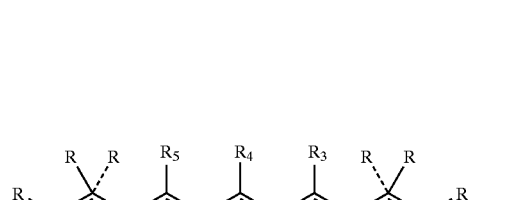

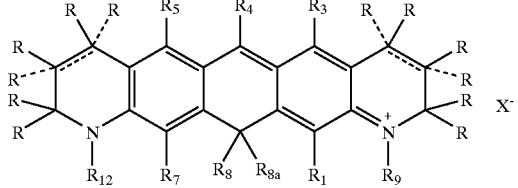

in which the dashed lines are optionally double bonds, in whose presence the radicals R bonded via a dashed line are absent, $R_1$, $R_3$, $R_4$, $R_5$, $R_6$, $R_7$, $R_8$, $R_{8a}$, $R_9$, $R_{11}$, $R_{12}$ and X are as defined above, and R, on each occurrence, can be identical or different and is defined as $R_1$–$R_7$ above.

The compounds preferably have a group capable of covalent coupling, e.g. —COOH, —NH$_2$, —OH or/and —SH. By means of this coupling group, the compound can be coupled to a carrier or/and to a biomolecule according to known methods. The carrier can consist of any material which is suitable, in particular for detection procedures, e.g. of porous glass, plastics, ion-exchange resins, dextrans, cellulose, cellulose derivatives or/and hydrophilic polymers. The biomolecules are preferably selected from peptides, polypeptides, nucleotides, nucleosides, nucleic acids, nucleic acid analogs or/and haptens.

Surprisingly, the absorption maxima and the fluorescence quantum yield are not significantly changed by coupling of the compounds according to the invention to the abovementioned carriers and biomolecules.

Actual examples of compounds according to the invention are shown in table 1 below.

TABLE 1

$\lambda_A$: absorption maximum
$\lambda_F$: fluorescence maximum
$Q_F$: fluorescence quantum yield in ethanol

| | Structure | $\lambda_A$/nm | $\lambda_F$/nm | $Q_F$/% |
|---|---|---|---|---|
| 1 Cp 149 | 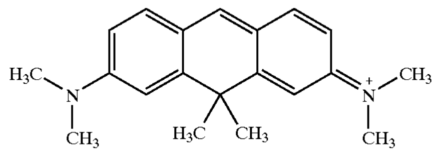 | 606 | 627 | 71 |
| 2 AZ 6 | 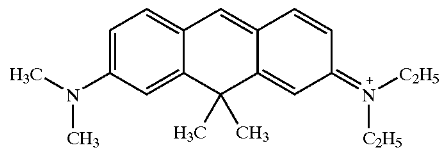 | 608 | 630 | 65 |
| 3 JA 261 | 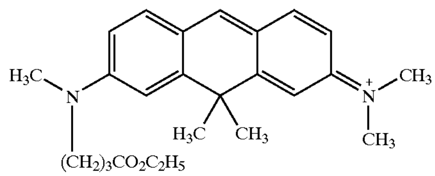 | 608 | 630 | 70 |
| 4 JA 262 | 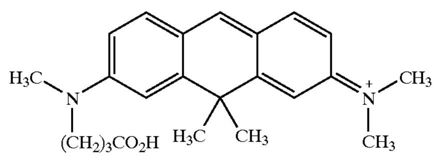 | 608 | 630 | 70 |
| 5 AZ 1 | 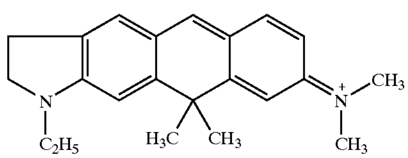 | 617 | 641 | 77 |
| 6 AZ 4 | 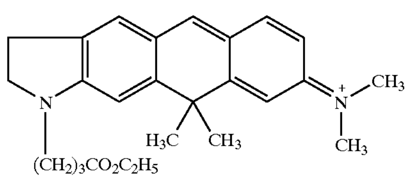 | 617 | 641 | 78 |
| 7 AZ 14 | 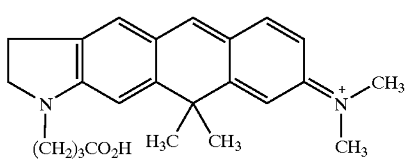 | 617 | 641 | 78 |
| 8 AZ 7 | 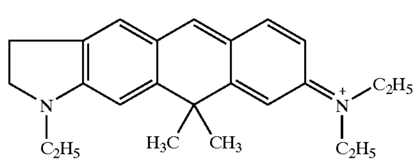 | 618 | 642 | 75 |

TABLE 1-continued $\lambda_A$: absorption maximum
$\lambda_F$: fluorescence maximum
$Q_F$: fluorescence quantum yield in ethanol

| | Structure | $\lambda_A$/nm | $\lambda_F$/nm | $Q_F$/% |
|---|---|---|---|---|
| 9 JA 260 | 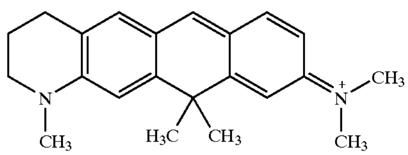 | 616 | 640 | 75 |
| 10 JA 264 | 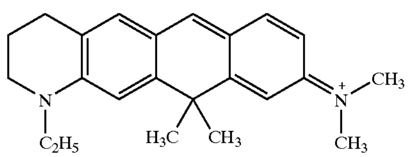 | 616 | 640 | 75 |
| 11 JA 263 | 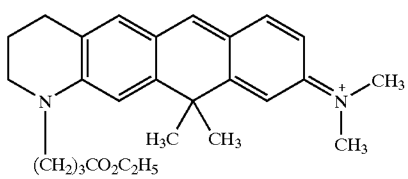 | 616 | 640 | 76 |
| 12 JA 266 | 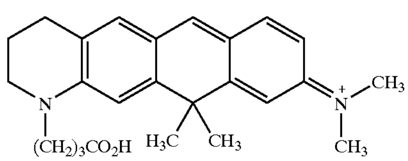 | 616 | 640 | 76 |
| 13 JA 265 | 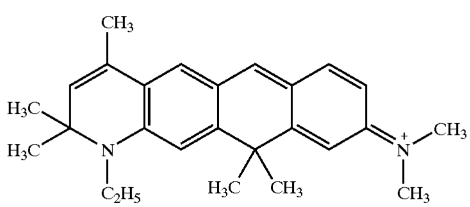 | 634 | 658 | 62 |
| 14 AZ 8 | 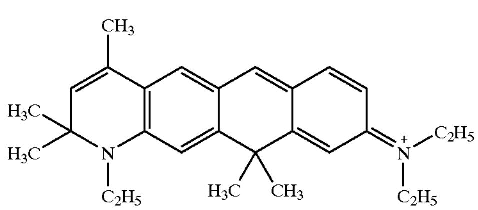 | 641 | 666 | 60 |
| 15 JA 267 | 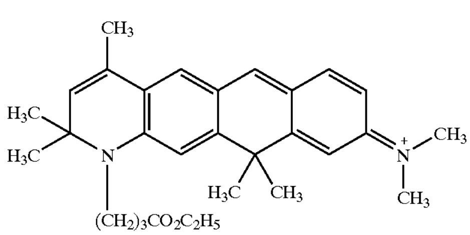 | 633 | 660 | 60 |

TABLE 1-continued

λ_A: absorption maximum
λ_F: fluorescence maximum
Q_F: fluorescence quantum yield in ethanol

| | Structure | $\lambda_A$/nm | $\lambda_F$/nm | $Q_F$/% |
|---|---|---|---|---|
| 16 JA 268 | 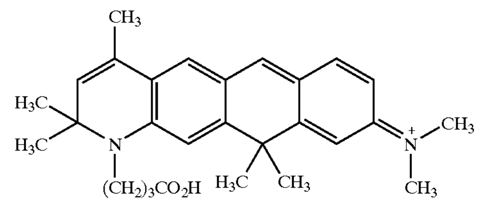 | 634 | 660 | 58 |
| 17 AZ 2 | 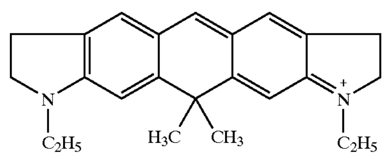 | 633 | 657 | 63 |
| 18 AZ 5 | 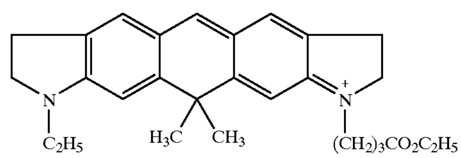 | 633 | 657 | 61 |
| 19 AZ 3 | 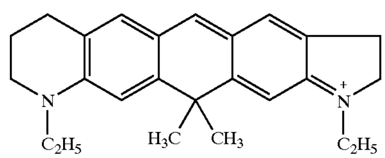 | 629 | 650 | 69 |
| 20 AZ 13 | 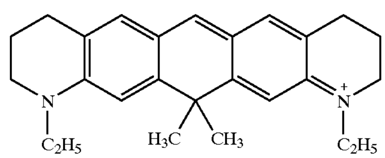 | 626 | 648 | 87 |
| 21 AZ 9 | 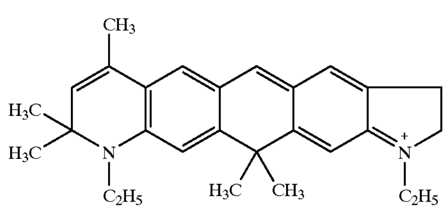 | 647 | 675 | 55 |
| 22 AZ 12 | 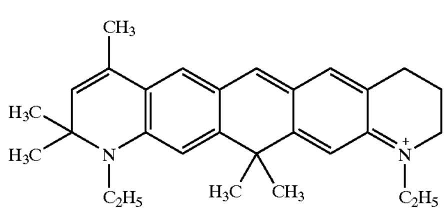 | 647 | 664 | 58 |
| 23 AZ 11 | 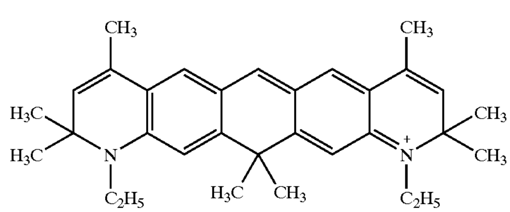 | 664 | 688 | 49 |

TABLE 1-continued

λ_A: absorption maximum
λ_F: fluorescence maximum
Q_F: fluorescence quantum yield in ethanol

| | Structure | $\lambda_A$/nm | $\lambda_F$/nm | $Q_F$/% |
|---|---|---|---|---|
| 24 JF 19 | 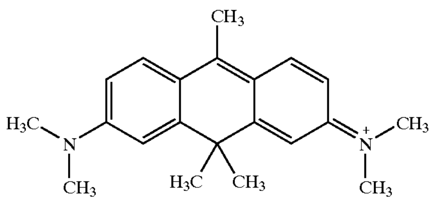 | 602 | 643 | 58 |
| 25 JF 20 | 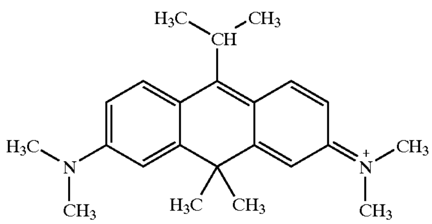 | 604 | 675 | 41 |
| 26 JF 18 | 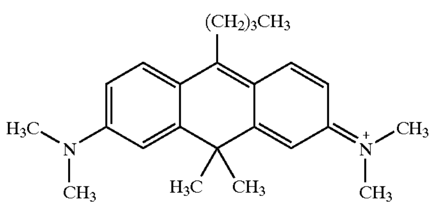 | 601 | 636 | 67 |
| 27 JF 16 | 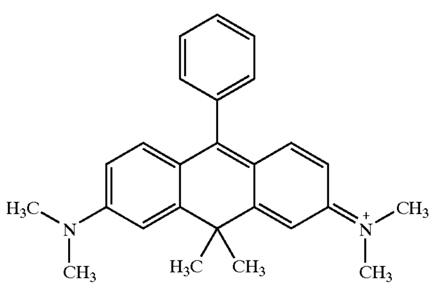 | 611 | 638 | 6 |
| 28 JF 21 | 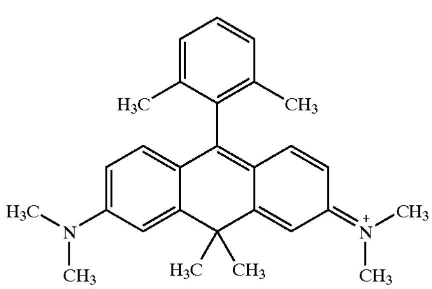 | 610 | 637 | 46 |
| 29 JF 22 | 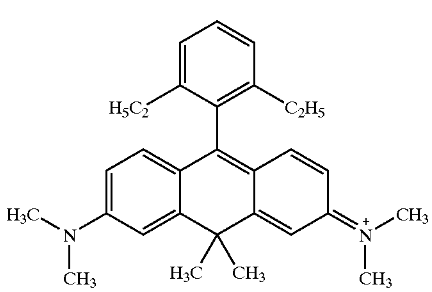 | 612 | 641 | 41 |

TABLE 1-continued
λ$_A$: absorption maximum
λ$_F$: fluorescence maximum
Q$_F$: fluorescence quantum yield in ethanol
| | Structure | λ$_A$/nm | λ$_F$/nm | Q$_F$/% |
|---|---|---|---|---|
| 30 JF 24 | 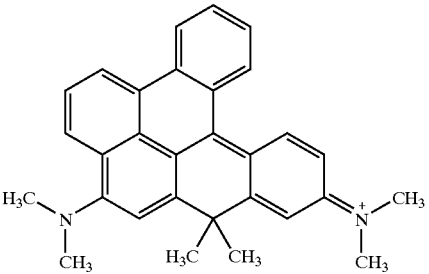 | 617 | 643 | 71 |
| 31 JF 25 | 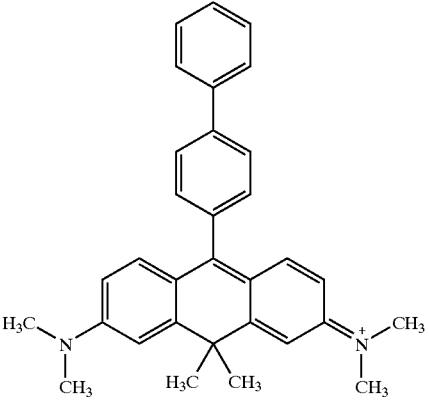 | 613 | 638 | 6 |
| 32 JF 26 | 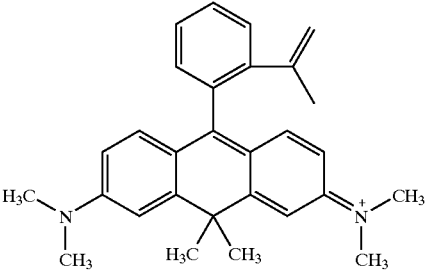 | 611 | 640 | 59 |
| 33 JF 17 | 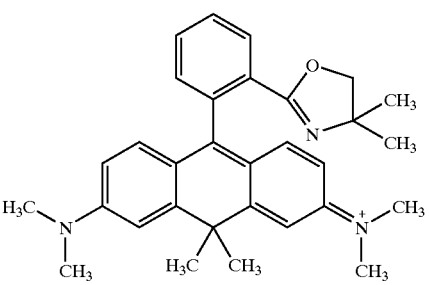 | 610 | 640 | 70 |

TABLE 1-continued
λ$_A$: absorption maximum
λ$_F$: fluorescence maximum
Q$_F$: fluorescence quantum yield in ethanol
| | Structure | λ$_A$/nm | λ$_F$/nm | Q$_F$/% |
|---|---|---|---|---|
| 34 JF 23 | 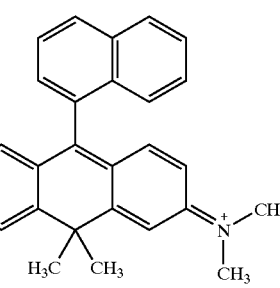 | 618 | 643 | 60 |
| 35 AZ 16 | 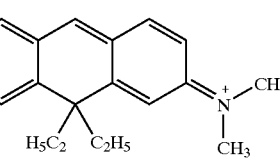 | 606 | 628 | 70 |
| 36 AZ 17 | 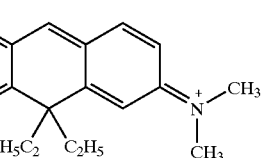 | 615 | 640 | 75 |
| 37 AZ 18 | 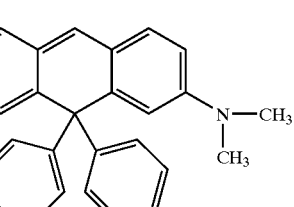 | 627 | 655 | 62 |
| 38 JF30 | 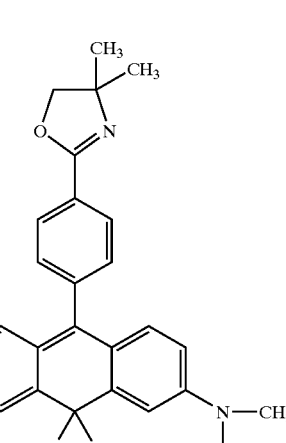 | 621 | 652 | 4 |

TABLE 1-continued
*λ*$_A$: absorption maximum
*λ*$_F$: fluorescence maximum
Q$_F$: fluorescence quantum yield in ethanol
| | Structure | λ$_A$/nm | λ$_F$/nm | Q$_F$/% |
|---|---|---|---|---|
| 39 JF 31 | 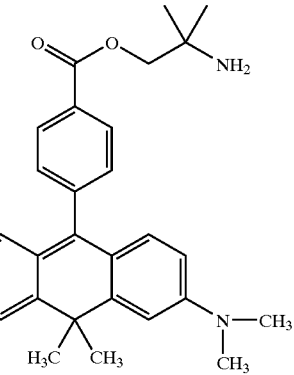 | 618 | 648 | 5 |
| 40 JF 32 | 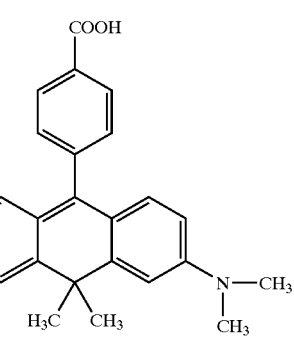 | 618 | 647 | 5 |
| 41 JF 34 | 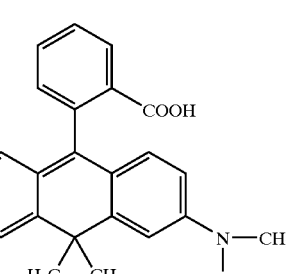 | 612 | 642 | 75 |
| 42 JF 35 | 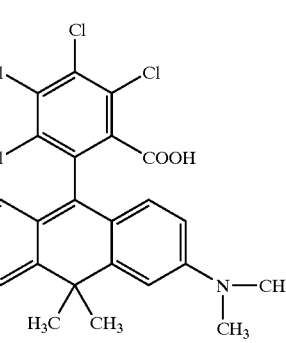 | 642 | 672 | 64 |

TABLE 1-continued

*λ*$_A$: absorption maximum
*λ*$_F$: fluorescence maximum
*Q*$_F$: fluorescence quantum yield in ethanol

| | Structure | $\lambda_A$/nm | $\lambda_F$/nm | $Q_F$/% |
|---|---|---|---|---|
| 43 JF 36 | | 632 | 662 | 85 |
| 44 JF 37 | | 662 | 692 | 60 |
| 45 JF 38 | | 653 | 683 | 70 |
| 46 JF 39 | | 683 | 713 | 45 |

TABLE 1-continued

λ_A: absorption maximum
λ_F: fluorescence maximum
Q_F: fluorescence quantum yield in ethanol

| Structure | $\lambda_A$/nm | $\lambda_F$/nm | $Q_F$/% |
|---|---|---|---|
| 47 JF 40 | 670 | 700 | 55 |
| 48 JF 41 | 700 | 730 | 40 |
| 49 JF 42 | 557 | 577 | 95 |
| 50 JF 43 | 632 | 660 | 80 |

A further object of the present invention consisted in making available a preparation process for carbopyronine compounds which can be carried out in a simple, environmentally compatible and inexpensive manner and which at least partially avoids the disadvantages of the known processes for the preparation of carbopyronines.

This object was achieved according to the invention by a process for the preparation of compounds of the general formula (I)

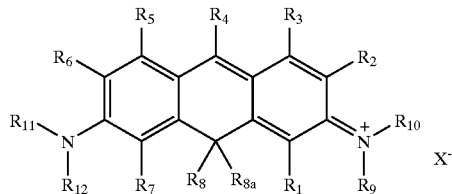

I where $R_1$–$R_{12}$ and X have the meanings indicated in claim 1, characterized in that a compound of the general formula (II)

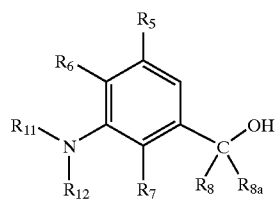

II in which $R_5$, $R_6$, $R_7$, $R_8$, $R_{8a}$, $R_{11}$ and $R_{12}$ are as defined above, or the dehydration product of II is reacted with a compound of the general formula III

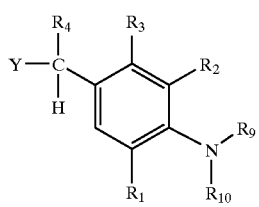

III in which $R_1$–$R_4$, $R_9$ and $R_{10}$ are as defined above and Y is a halogen, in particular bromine, a hydroxyl or thio group, in a suitable solvent, under acidic conditions and in the presence of a catalyst and the compound formed by ring closure between the compounds II or their dehydration product and III is reacted by oxidation to give the structure I.

In the process, it is possible to use all suitable solvents which are compatible with the starting materials, the products and the catalyst, preferably boron trichloride. The solvent is preferably a nonpolar solvent, in particular methylene chloride, 1,2-dichloroethane or chloroform.

The acids employed can be customary acids. The acid is preferably an inorganic acid such as sulfuric acid, phosphoric acid or polyphosphoric acid.

The oxidants used can likewise be customary oxidants. The oxidant tetrabutylammonium(meta)periodate is preferred.

It is particularly advantageous that the process can be carried out without isolation of intermediates. This leads to a reduction in the expenditure of time, labor and material.

The invention is illustrated in greater detail by the examples below. The FIGS. 1, 2, 3 and 4 show the absorption and fluorescence spectra of the compounds according to the invention AZ 2 (17), AZ 13 (20), JA 268 (16) and AZ11 (23).

EXAMPLES

A. Preparation Process According to the Invention for Carbopyronine Compounds

In the process according to the invention, 4-N,N-dimethylaminobenzylsulfanilic acid, which is used in the process according to Aaron and Barker (J. Chem. Soc. (1963), 2655) is replaced by 4-hydroxymethyl-N,N-dimethylaniline and reacted with the isopropenyl derivative to give the carbopyronine in the presence of boron trichloride solution as a catalyst. The reaction mixture can be reacted with concentrated sulfuric acid to give the leuko base of the dye without isolation of the intermediate. The oxidant lead dioxide used in Aaron and Barker (loc. cit.) is replaced by tetrabutylammonium(meta)periodate. To this end, the ethanolic solution of oxidant and leuko base is heated to boiling, it being possible to detect by thin-layer chromatography that the oxidation is already complete after a few minutes.

After the oxidation, the carbopyronine is precipitated from ethanolic solution as a poorly soluble perchlorate by addition of 10% strength sodium perchlorate solution and slow dropwise addition of water.

The novel synthesis route can be employed universally. The corresponding alcohols can be obtained from aniline, indoline, tetrahydroquinoline and 1,2-dihydroquinoline derivatives by a Vilsmaier synthesis with subsequent reduction and these can be reacted with an isopropenyl derivative to give the dye. Unlike the synthesis of Aaron and Barker, the synthesis proceeds in one step, i.e. isolation of intermediates is not necessary.

The synthesis procedures for the compounds JA 261, JA 262, AZ 4, AZ 14, JA 267, JA 268, JF 19, JF 22 and JF 17 are presented below.

B. Synthesis Examples

Compound JA 261

1 g (4 mmol) of ethyl N-methyl-N-(4-hydroxymethylphenyl)-4-aminobutyrate and 0.71 g (4.4 mmol) of 3-(isopropenyl)-N,N-dimethylaniline are dissolved in 20 ml of methylene chloride. 4 ml of a 1 molar $BCl_3$ solution (in methylene chloride) are slowly added with stirring and ice cooling. The solution is stirred overnight at room temperature. The reaction mixture is then added dropwise to 20 g of concentrated sulfuric acid, which is cooled in an ice/methanol bath. The mixture is stirred until a homogeneous solution is present. The methylene chloride is distilled off on a rotary evaporator. The sulfuric acid solution is stored overnight in a refrigerator. The solution is then poured onto ice and neutralized with dilute sodium hydroxide solution. The aqueous solution is extracted with chloroform. The combined organic phases are dried over sodium sulfate, filtered and concentrated to dryness on a rotary evaporator. The residue is taken up in 200 ml of ethanol and treated with 10 drops of 60% strength perchloric acid and 0.17 g (0.39 mmol) of tetrabutylammonium(meta)periodate. The solution is heated to reflux for 30 min. The cooled solution is added dropwise to a solution of 20 g of sodium perchlorate in 1 l of water. The mixture is stirred overnight. The green, lustrous precipitate is filtered off and dried over phosphorus pentoxide in a desiccator.

Yield: 0.56 g $^1$H-NMR data in $CDCl_3$:

δ 1.25 (T, 3H, —$CH_3$); 1.7 (S, 6H, —$CH_3$); 2.0 (QI, 2H, —$CH_2$—); 2.5 (T, 2H, —$CH_2$—); 3.3 (S, 9H, N—$CH_3$); 3.7 (T, 2, —$CH_2$—); 4.15 (Q, 2H, N—$CH_2$—); 6.85 (DvD, 2H, ArH); 7.05 (D, 1H, ArH); 7.2 (D, 1H, ArH); 7.65 (D, 2H, Ar—H); 8.0 (S, 1H, —CH=)

Compound JA 262

100 mg of JA 261 are dissolved in a mixture of 20 ml of acetone, 40 ml of water and 2 ml of 2 N hydrochloric acid. The solution is heated to reflux (internal temperature: 64° C.). After 24 h, the solution is cooled and treated with 100 ml of 10% strength aqueous sodium perchlorate solution. The precipitate is filtered off and dried.

Yield: 0.04 g.

Compound AZ 4

1.00 g (4.25 mmol) of ethyl 4-(5-hydroxymethylindolin-1-yl)butyrate and 0.76 g (4.25 mmol) of 3-(isopropenyl)-N,N-dimethylaniline are dissolved in 15 ml of methylene chloride and treated dropwise with 4.25 ml (4.25 mmol) of a 1 molar solution of boron trichloride in hexane with ice cooling. The reaction mixture is stirred at room temperature for 30 min. The reaction mixture is then added dropwise to 10 ml of concentrated sulfuric acid and stirred at room temperature for 1 h. The deep red-colored reaction mixture is added dropwise to 100 ml of ice-cold ethanol, treated with 0.78 g (1.8 mmol) of tetrabutylammonium(meta)periodate and heated to boiling for 3 min. It is allowed to cool to room temperature and is treated with 50 ml of 20% strength sodium perchlorate solution. 300 ml of water are then added dropwise to precipitate the dye completely. The crystalline product is filtered off and dried in vacuo in a desiccator using SICAPENT®.

Yield: 0.7 g $^1$H-NMR data in acetone-$d_6$:

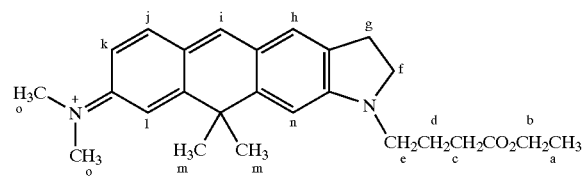

δ 0.9 (T, 3H, —CH$_3$ a); 1.7 (S, 6H, —CH$_3$ m); 2.47 (T, 2H, —CH$_2$-c); 3.22 (T, 2H, —CH$_2$— g); 3.34 (S, 6H, N—CH$_3$ o); 3.8 (T, 2, —CH$_2$— e); 4.09 (T, 2H, —CH$_2$— f); 4.42 (Q, 2H, —CH$_2$— b); 6.95 (DvD, 1H, ArH k); 7.22 (D, 1H, ArH l); 7.3 (S, 1H, ArH n); 7.7 (D, 1H, Ar—H j); 8.08 (S, 1H, —CH=i)

Compound AZ 14

4 g (8 mmol) of AZ 4 are dissolved in 30 ml of water and 20 ml of acetone and treated with 1 ml of 2 N hydrochloric acid. The reaction mixture is heated to reflux for 18 h. It is treated with 50 ml of chloroform and the organic phase is separated off. After extraction with chloroform a further three times, the combined organic phases are washed with water and dried over sodium sulfate. The dye solution is concentrated to dryness on a rotary evaporator and then purified by column chromatography.

$^1$H-NMR data in acetone-$d_6$:

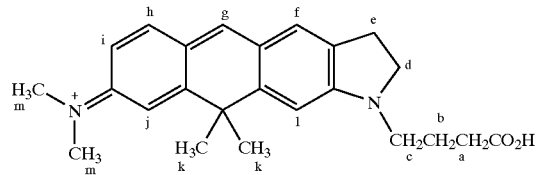

δ 1.72 (S, 6H, —CH$_3$ k); 2.0 (M, 2H, —CH$_2$— b); 2.49 (T, 3H, —CH$_2$— a); 3.25 (T, 2H, —CH$_2$— e); 3.34 (S, 6H, —CH$_3$ m); 3.81 (T, 2, —CH$_2$— c); 4.11 (T, 2H, —CH$_2$— d); 6.95 (DvD, 1H, ArH i); 7.22 (D, 1H, ArH j); 7.3 (S, 1H, ArH l); 7.42 (D, 1H, Ar—H f); 7.7 (D, 1H, ArH h); 8.1 (S, 1H, —CH=g)

Compound JA 267

1.2 g (3.8 mmol) of ethyl 4-(6-hydroxymethyl-2,2,4-trimethyl-1,2-dihydroquinol-1-yl)butyrate and 0.68 g (3.8 mmol) of 3-(isopropenyl)-N,N-dimethylaniline are dissolved in 30 ml of methylene chloride. 4 ml of a 1 molar BCl$_3$ solution in methylene chloride are added slowly with stirring and ice cooling. The solution is stirred at room temperature for 20 min. The reaction mixture is then added dropwise to 20 ml of conc. sulfuric acid. It is stirred until a homogeneous solution is present. The methylene chloride is distilled off on a rotary evaporator and the sulfuric acid solution is stirred at room temperature for 1 h. The residue is taken up in 400 ml of ice-cooled ethanol. 1.2 g (2.7 mmol) of tetrabutylammonium(meta)periodate are added thereto. The solution is briefly heated to boiling, cooled and treated with 200 ml of a 20% strength sodium perchlorate solution. 500 ml of water are then added dropwise. The precipitate is filtered off and dried in a desiccator.

Compound JA 268

1.8 g of JA 267 are heated to reflux for 6 h in a mixture of 50 ml of acetone, 50 ml of water and 5 ml of 2 N hydrochloric acid. The solvent is distilled off and the residue is purified by chromatography.

Compound JF 19

0.27 ml (0.81 mmol) of a 3 M methylmagnesium bromide solution in diethyl ether are added dropwise within an argon protective gas atmosphere at room temperature to a solution of 50 mg (0.16 mmol) of 2,10-bis(dimethylamino)anthrone in 10 ml of dry tetrahydrofuran. After reaction is complete, the reaction mixture is cooled in an ice-water bath, dissolved in 50 ml of ethanol and acidified with trifluoroacetic acid. This solution is suspended in a mixture of 50 ml of chloroform and 50 ml of water. The organic phase is separated off, concentrated to dryness on a rotary evaporator and dissolved in ethanol. The solution is then added dropwise to 100 ml of aqueous 25% strength sodium perchlorate solution. After addition is complete, a further 300 ml of water are added dropwise. The dye precipitated is filtered and dried in vacuo.

Yield: 0.04 g

Compound JF 22

Under protection by argon, 11 mg (1.6 mmol) of lithium powder (0.5% sodium, Metallgesellschaft) are suspended in 2 ml of dry diethyl ether. A solution of 0.17 g (0.8 mmol) of 1-bromo-2,6-diethylbenzene in 4 ml of diethyl ether is added dropwise to this suspension with stirring. After addition is complete, the mixture is stirred at room temperature for 15 min. The suspension is filtered through glass wool in order to remove the remaining residues of lithium. The solution thus obtained is added dropwise at room temperature to a solution of 50 mg (0.16 mmol) of 2,10-bis(dimethylamino)anthrone in 10 ml of dry tetrahydrofuran. After reaction is complete, the reaction mixture is cooled in an ice-water bath, dissolved in 50 ml of ethanol and acidified with trifluoroacetic acid. This solution is suspended in a mixture of 50 ml of chloroform and 50 ml of water. The organic phase is separated off, concentrated to dryness on a rotary evaporator and purified by column chromatography on silica gel. After the dye fraction has been concentrated to dryness on a rotary evaporator, it is dissolved in ethanol and then added dropwise to 100 ml of aqueous 25% strength sodium perchlorate solution. A further 300 ml of water are then added dropwise. The dye precipitated is filtered and dried in vacuo.

Yield: 0.02 g

Compound JF 17

0.14 g (0.55 mol) of 2-(2-bromophenyl)-4,4-dimethyl-2-oxazoline is dissolved in 7.5 ml of tetrahydrofuran under protective gas (argon) and cooled to −78° C. 0.7 ml (1.1 mmol) of a 1.6 M solution of t-butyllithium in hexane are added dropwise to this solution such that the temperature remains below −75° C. After addition is complete, the solution is stirred for 15 min. 34 mg (0.11 mmol) of 2,10-bis(dimethylamino)anthrone in 2 ml of dry tetrahydrofuran are added to this solution. The temperature should not exceed −70° C. in the course of this. The mixture is then warmed to −60° C. and stirred for 3 h. The cooling bath is removed and the mixture is allowed to warm to room temperature. After 24 h, the reaction mixture is cooled in an ice-water bath,. dissolved in 50 ml of ethanol and acidified with trifluoroacetic acid. This solution is suspended in a mixture of 50 ml of chloroform and 50 ml of water. The organic phase is separated off, concentrated to dryness on a rotary evaporator and purified by column chromatography. The dye fraction is concentrated to dryness on a rotary evaporator, taken up in ethanol and subsequently added dropwise to 100 ml of aqueous 25% strength sodium perchlorate solution. After addition is complete, a further 300 ml of water are added dropwise. The dye precipitated is filtered and dried in vacuo.

Compound AZ 18

1st Stage 3-(N,N-Dimethylamino)triphenylcarbinol 2.8 g (0.12 mol) of magnesium and 10 ml of diethyl ether (absolute) are treated with 2.6 g (0.02 mol) of broinobenzene. In order to start the reaction, the mixture is slightly warmed. The start of the reaction can be detected by the turbidity of the reaction mixture. 16.2 g (0.1 mol) of bromobenzene are then dissolved in 15 ml of ether and added dropwise to the reaction mixture. It is heated to reflux for 1 h, the magnesium almost completely dissolving. After cooling in an ice bath, a solution of 10 g (0.055 mol) of methyl 3-dimethylaminobenzoate in 15 ml of absolute ether is added dropwise. After the addition, the reaction mixture is heated to reflux for 2 h, cooled and hydrolyzed dropwise with water. 50 ml of water and 50 ml of ether are added and the mixture is treated with saturated ammonium chloride solution until the white precipitate has dissolved again. The aqueous phase is extracted with ether. The combined organic phases are washed with saturated sodium hydrogencarbonate solution and with water. The solution is then dried over sodium sulfate and the solvent is distilled off. The residual pale yellow oil can be used directly for the subsequent reaction.

2nd Stage

AZ 18

0.6 g (3 mmol) of N,N-dimethyl-4-hydroxymethylaniline and 0.9 g (3 mmol) of 3-(N,N-dimethylamino) triphenylcarbinol are dissolved in 30 ml of methylene chloride. 4 ml of a 1 molar $BCl_3$ solution in methylene chloride are slowly added with stirring and ice cooling. The solution is stirred at room temperature for 2 h. The reaction mixture is then added dropwise to 20 ml of 70% strength sulfuric acid. The methylene chloride is distilled off on a rotary evaporator and the sulfuric acid solution is stirred at room temperature for 20 h. The residue is slowly dissolved in 100 ml of ice-cooled ethanol. 1.2 g (2.7 mmol) of tetrabutylammonium(meta)periodate are added thereto. The solution is briefly heated to boiling, cooled and treated with 100 ml of a 20% strength sodium perchlorate solution. 250 ml of water are then added dropwise. The precipitate is filtered off and dried in a desiccator.

Compound JF 30

1.85 ml (3.05 mmol) of a 15% strength t-butyllithium solution (in n-pentane) are added at −78° C. to a solution of 0.39 g (1.53 mmol) of 2-(4-bromophenyl)-4,4-dimethyl-2-oxazoline in 20 ml of dry tetrahydrofuran such that the temperature remains below −70° C. After complete addition, 150 mg (0.48 mmol) of 3,6-bis(dimethylamino)anthrone in 30 ml of dry tetrahydrofuran are added such that the temperature remains below −60° C. The solution is allowed to warm to room temperature and is stirred at room temperature for 18 h. The reaction mixture is cooled in an ice-water bath, dissolved in 50 ml of ethanol and acidified with trifluoroacetic acid. This solution is suspended in a mixture of 50 ml of chloroform and 50 ml of water. The organic phase is separated off, concentrated to dryness on a rotary evaporator, and purified by column chromatography on silica gel. The dye is eluted using 15% strength ethanolic chloroform. After the product phase has been concentrated to dryness on a rotary evaporator, it is dissolved in ethanol and then added, dropwise to 100 ml of aqueous 25% strength sodium perchlorate solution. After addition is complete, a further 300 ml of water are added dropwise. The dye precipitated is filtered and dried over phosphorus pentoxide in a vacuum desiccator.

Yield: 50% (cryst. substance after chromatography)

Compound JF 31

80 mg (0.14 mmol) of JF 30 are heated under reflux for 40 min in 10 ml of a 1:3 mixture of 2 M hydrochloric acid and acetone. The mixture is allowed to cool and is suspended in 50 ml of a 1:1 mixture of chloroform and water. The water phase is neutralized with saturated sodium hydrogencarbonate solution. The organic phase is separated off and the aqueous is extracted a number of times with 20% strength ethanolic chloroform. The combined organic phases are concentrated on a rotary evaporator and purified by column chromatography on silica gel. The dye is eluted using 20% strength ethanolic chloroform. After the product phase has been concentrated to dryness on a rotary evaporator, it is dissolved in ethanol and then added dropwise to 100 ml of aqueous 25% strength sodium perchlorate solution. After addition is complete, a further 300 ml of water are added dropwise. The dye precipitated is filtered and dried over phosphorus pentoxide in a vacuum desiccator.

Yield: 72% (cryst. substance after chromatography)

Compound JF 32

70 mg (0.12 mmol) of JF 31 are heated to reflux for 1 h in a 10% strength sodium hydroxide solution in 1:1 ethanol and water. The mixture is allowed to cool and is suspended in a 1:1 mixture of chloroform and water. It is adjusted to pH=8 using trifluoroacetic acid and the organic phase is separated off. The aqueous phase is extracted a number of times with 20% strength ethanolic chloroform. This extraction is repeated until there is barely still dye in the aqueous phase (testing by means of acidification). The combined organic phases, are adjusted to pH=2 using trifluoroacetic acid, concentrated on a rotary evaporator and purified by column chromatography on silica gel. The dye is eluted using 10% strength ethanolic chloroform. After the product phase has been concentrated to dryness on a rotary evaporator, it is dissolved in ethanol and then added dropwise to 100 ml of aqueous 25% strength sodium perchlorate solution. After addition is complete, a further 300 ml of water are added dropwise. The dye precipitated is filtered and dried over phosphorus pentoxide in a vacuum desiccator.

Yield: 57% (cryst. substance after chromatography)

Compound JF 42

70 mg (0.12 mmol) of JF 17 are heated to reflux for 1 h in 30 ml of a solution of 3 g of sodium hydroxide in ethanol/water (1:1). The solution is allowed to cool and is neutralized using semiconcentrated hydrochloric acid. The dye is then precipitated by dropwise addition of water. The product is filtered off and dried in a vacuum desiccator over phosphorus pentoxide.

Compound JF 36

25.3 g (0.1 mol) of 6-(2-carboxybenzoyl)-N-ethyl-1,2,3,4-tetrahydroquinoline and 20.1 (0.1 mol) of N-ethyl-7-isopropenyl-1,2,3,4-tetrahydroquinoline are dissolved in 500 ml of dichloromethane and treated with 60 g of phosphorus pentoxide. The mixture is heated under reflux for 2 h, allowed to cool and the solvent is distilled off in vacuo.

The residue is treated with conc. sulfuric acid. This solution is stirred at room temperature for 30 min. After this, the sulfuric acid solution is added to 1 000 ml of ice-cooled ethanol and treated dropwise with 50 ml of 60% strength perchloric acid and 5 l. The dye precipitated is filtered off and dried over phosphorus pentoxide in a vacuum desiccator.

Compound JF 37

39.1 g (0.1 mol) of 6-(2-carboxy-3,4,5,6-tetrachlorobenzoyl)-N-ethyl-1,2,3,4-tetrahydroquinoline and 20.1 (0.1 mol) of N-ethyl-7-isopropenyl-1,2,3,4-tetrahydroquinoline are dissolved in 500 ml of dichloromethane and treated with 60 g of phosphorus pentoxide. The mixture is heated under reflux for 2 h, allowed to cool and the solvent is distilled off in vacuo. The residue is treated with conc. sulfuric acid. This solution is stirred at room temperature for 30 min. After this, the sulfuric acid solution is added to 1 000 ml of ice-cooled ethanol and treated dropwise with 50 ml of 60% strength perchloric acid and 5 l. The dye precipitated is filtered off and dried over phosphorus pentoxide in a vacuum desiccator.

C. Examples of Conjugate Formation

JA 262 Active Ester 0.1 mmol of JA 262 is dissolved in 20 ml of acetonitrile with 0.2 mmol of N-hydroxysuccinimide and 0.2 mmol of dicyclohexylcarbodiimide. The solution is stirred at room temperature for 4 h and the product mixture is concentrated on a rotary evaporator. Purification is carried out by chromatography (HPLC, RP 18).

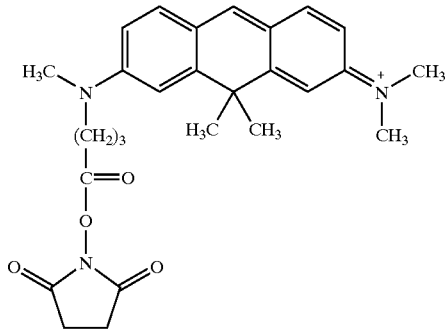

JF 43 Maleimide 100 mg of JF 43 (0.16 mmol) are dissolved in 10 ml of dried DMSO and treated with 100 mg (1 mmol) of maleic anhydride. The solution is stirred at room temperature for 24 h. 50 ml of 10% strength aqueous sodium perchlorate solution are added dropwise and the solid precipitated is filtered off. The solid is suspended in 5 ml of acetic anhydride with 25 mg of sodium acetate and heated to 80° C. for 30 min. The mixture is cooled and 30 ml of 10% strength aqueous sodium perchlorate solution are added dropwise. The solid is filtered off and dried.

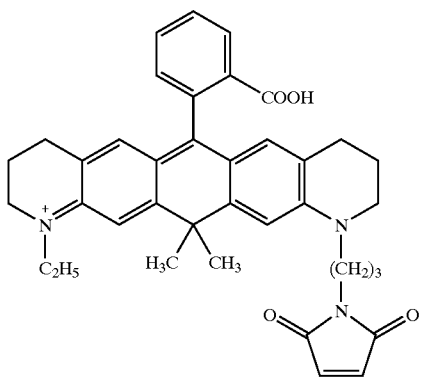

JF 43-cysteine Conjugate 70 mg (0.1 mmol) of JF 43 maleimide are dissolved in 20 ml of ethanol and treated in portions with 12 mg (0.1 mmol) of cysteine. The solution is stirred at room temperature for 30 min. After this, 50 ml of 10% strength aqueous sodium perchlorate solution are added dropwise and the solid precipitated is filtered off and dried.

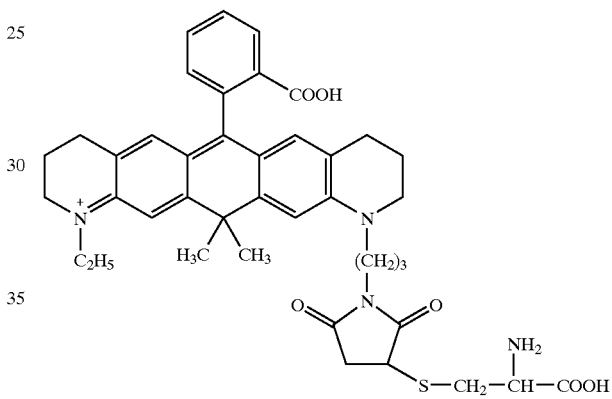

JA 262-dUTP Conjugate

10 μmol of 5-(3-aminoallyl)-dUTP are dissolved in 0.5 ml of 0.1 M sodium borate buffer (pH 8) and treated with a solution of 5 μmol of JA 262 active ester in 1 ml of amine-free dimethylformamide. The solution is stirred at room temperature for 15 h. The solvents are distilled off in vacuo and the residue is purified by chromatography (RP 18).

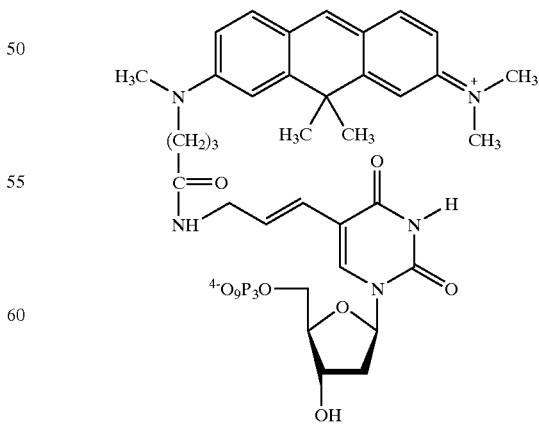

JA 262-digoxin-3-carboxymethyl Ether-diaminodioxaoctane Conjugate (Dig-CME-DADOO)

0.02 mmol of JA 262 active ester are stirred in acetonitrile at room temperature for 18 h with 0.02 mmol of Dig-CME-DADOO. The solvent is distilled off and the residue is purified by chromatography.

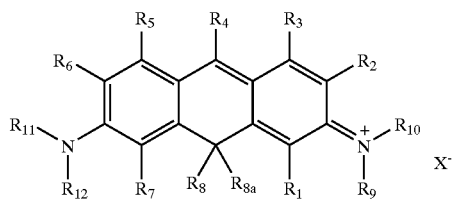

What is claimed is:

1. In an immunoassay or nucleic acid hybridization method for the detection of an analyte in a sample, the improvement which comprises using a labeled receptor for the analyte wherein the label is a compound of the general formula I

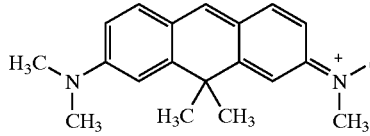

wherein:
$R_1$, $R_2$, $R_3$, $R_4$, $R_5$, $R_6$ and $R_7$ are, independently, hydrogen, halogen, a hydroxyl, amino, sulfo, carboxyl or aldehyde group, a substituted or unsubstituted, saturated or unsaturated straight chain, branched or cyclic alkyl group having up to 20 carbon atoms, or a substituted or unsubstituted, aromatic ring system; or two or more adjacent $R_1$–$R_7$ groups, together may form a ring system which containing one or more multiple bonds;

$R_8$ and $R_{8a}$ are, independently, a saturated or unsaturated, straight-chain, branched or cyclic alkyl group having up to 20 carbon atoms, or $R_8$ and $R_{8a}$, together, can form a ring system of one or more rings;

$R_9$, $R_{10}$, $R_{11}$ and $R_{12}$, are independently, hydrogen, a substituted or unsubstituted, saturated or unsaturated, straight-chain, branched or cyclic alkyl group having up to 20 carbon atoms, a polyether, substituted or unsubstituted phenyl or substituted or unsubstituted phenylalkyl having 1–3 carbon atoms in the alkyl chain, provided that any of these groups may optionally contain one or more atoms selected from the group consisting of oxygen, sulfur and nitrogen atoms; or two or more adjacent $R_9$–$R_{12}$ groups, together, may form a ring system which can contain one or more multiple bonds; with the proviso that if $R_1$–$R_3$ and $R_5$–$R_7$ are hydrogen and $R_8$, $R_{8a}$ and $R_9$–$R_{12}$ are methyl, then $R_4$ is not one of hydrogen, hydroxyl, methyl, isopropyl, t-butyl, phenyl, o-tolyl, p-tolyl, 2,6-dimethylphenyl, 2-t-butylphenyl, 2-isopropenylphenyl and 4-dimethylaminophenyl;

wherein either or both of the groups —N($R_{11}$)($R_{12}$) and =N($R_9$)($R_{10}$) can be replaced by either —O$R_9$ or =O;

and X represents a species of anion present for charge equalization.

2. The method according to claim 1, wherein $R_1$–$R_7$ are, optionally, substituted by a member selected from the group consisting of halogens, hydroxyl, amino, sulfo, phospho, carboxyl, aldehyde, $C_1$–$C_4$-alkoxy, and $C_1$–$C_4$-alkoxycarbonyl groups.

3. The method according to claim 1, wherein $R_8$–$R_{8a}$ are, optionally, substituted with a member selected from the group consisting of halogens, hydroxyl, amino, sulfo, phospho, carboxyl, aldehyde, $C_1$–$C_4$-alkoxy and $C_1$–$C_4$-alkoxycarbonyl groups.

4. The method according to claim 1, wherein $R_9$, $R_{10}$, $R_{11}$ and $R_{12}$ are, optionally, substituted with a member selected from the group consisting of halogens, hydroxyl, amino, sulfo, phospho, carboxyl, carbonyl, alkoxy and alkoxycarbonyl groups.

5. The method as claimed in claim 1, wherein the compound I is covalently coupled to a receptor specific for an analyte to be detected.

6. The method as claimed in claim 1, wherein the detection procedure is selected from nucleic acid hybridization procedures and immunochemical procedures.

7. A compound of the general formula I

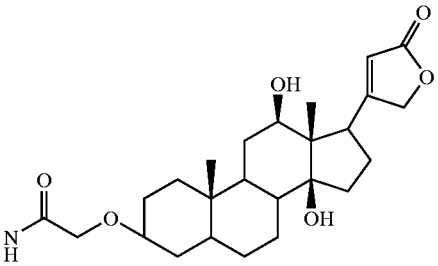

wherein $R_1$–$R_{12}$ and X are defined as in claim 1, with the proviso that if $R_1$–$R_3$ and $R_5$–$R_7$ are hydrogen and $R_8$, $R_{8a}$ and $R_9$–$R_{12}$ are methyl, then $R_4$ is not one of hydrogen, hydroxyl, methyl, isopropyl, t-butyl, phenyl, o-tolyl, p-tolyl, 2,6-dimethylphenyl, 2-t-butylphenyl, 2-isopropenylphenyl and 4-dimethylaminophenyl, and wherein one or more ring systems are formed by $R_6$ bridging with $R_{11}$, $R_7$ bridging with $R_{12}$; $R_1$ bridging with $R_9$ and/or $R_2$ bridging with $R_{10}$.

8. The compound according to claim 7, wherein the ring system formed by bridging $R_6$ with $R_{11}$, $R_7$ with $R_{12}$, $R_1$ with $R_9$ or $R_2$ with $R_{10}$ contains a 5- or 6-membered ring which contain one or more multiple bonds.

9. The compound according to claim 7, wherein $R_4$ is hydrogen, $C_1$–$C_6$-alkyl or an aromatic ring system.

10. The compound according to claim 7, wherein $R_8$ and $R_{8a}$ are, independently, methyl, ethyl or phenyl.

11. The compound according to claim 7, which corresponds to one of the general formulae IVa to IVe as follows:

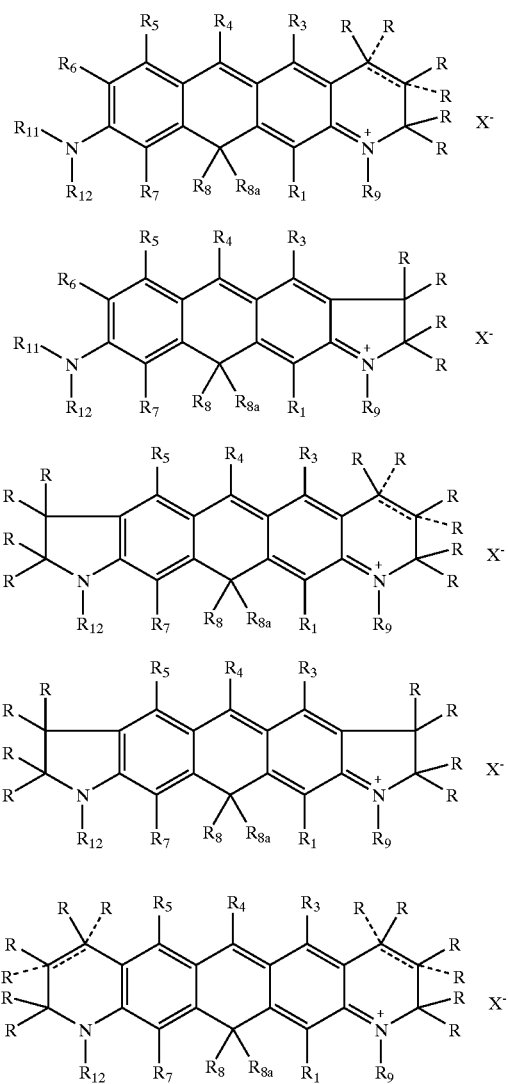

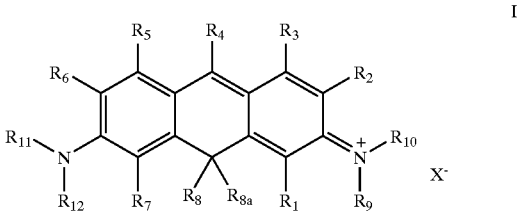

in which the broken lines represent optional double bonds, and when the double bond is present in the ring the radicals R bonded via a broken line are absent; $R_1$, $R_3$, $R_4$, $R_5$, $R_6$, $R_7$, $R_{8a}$, $R_9$, $R_{11}$, $R_{12}$ and X are as previously defined, and R in each occurrence, can be identical or different and is defined as $R_1$–$R_7$.

12. The compound according to claim 7 further comprising a group capable of covalent coupling the compound to a biomolecule.

13. The compound according to claim 12, wherein the coupling group is selected from the group consisting of —COOH, —NH2, —OH and —SH.

14. The compound according to claim 12 which is coupled to at least one of a carrier and a biomolecule via one or more coupling groups.

15. The compound according to claim 14, wherein the carrier is selected from the group consisting of porous glass, ion exchange resins, dextrans, cellulose, cellulose derivatives and hydrophilic polymers.

16. The compound according to claim 14, wherein the biomolecule is selected from the group consisting of at peptides, polypeptides, nucleotides, nucleosides, nucleic acids, nucleic acid analogs and haptens.

17. A process for the preparation of compounds of the general formula I wherein $R_1$–$R_{12}$ and X are defined as in claim 1, comprising the steps of:

reacting one of a compound of the general formula II

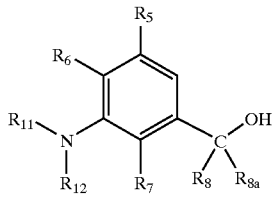

in which $R_5$, $R_6$, $R_7$, $R_8$, $R_{8a}$, $R_{11}$, $R_{12}$ are as previously defined, or the dehydration product of II, with a compound of the general formula III

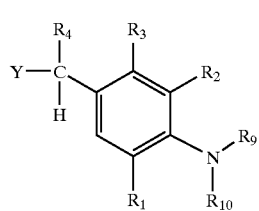

in which $R_1$–$R_4$, $R_9$ and $R_{10}$ are as previously defined and Y is a halogen, in a suitable solvent, under acidic conditions and in the presence of a catalyst; and reacting the compound formed by ring closure between one of the compound II or its dehydration product, and the compound III, by oxidation into the compound I.

18. The process according to claim 17, wherein the solvent is a nonpolar solvent, selected from one of methylene chloride, 1,2-dichloroethane or chloroform.

19. The process according to claim 17, wherein the catalyst is boron trichloride.

20. The process according to claim 17, wherein the acid is selected from one of sulphuric acid, phosphoric acid or polyphosphoric acid.

21. The process according to claim 17, wherein the oxidant is tetrabutylammonium(meta)periodate.

22. The process according to claim 17, wherein the compound (I) is obtained in a one-step process and without isolation of intermediates.

23. The method of claim 1, wherein the alkyl groups include at least one of phenyl and heteroaryl radicals as a substituent.

24. The method of claim 23, wherein the aromatic ring system includes at least one heteroatom selected from oxygen, sulfur or nitrogen atoms and two or more substituents.

25. The method of claim 1, wherein the saturated or unsaturated, straight-chain, branched or cyclic alkyl group having up to 20 carbon atoms is selected from the group consisting of at methyl, ethyl, propyl and butyl.

26. The method of claim 1, wherein the aromatic ring system contains at least one of a heteratom selected from oxygen, sulfur or nitrogen atoms and one or more substituents.

27. The process of claim 17, wherein the halogen is selected from the group of bromine, chorine or iodine.

28. A conjugate for the detection of an analyte comprising a compound according to claim 7, which is covalently coupled to a receptor specific for an analyte to be detected.

* * * * *